United States Patent
Snowden et al.

(10) Patent No.: US 7,524,983 B2
(45) Date of Patent: Apr. 28, 2009

(54) CATALYTIC SCRIABINE REACTION

(75) Inventors: Roger Snowden, Viry (FR); Anthony Birkbeck, Geneva (CH); Gary Womack, Hopewell, NJ (US)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 11/861,078

(22) Filed: Sep. 25, 2007

(65) Prior Publication Data

US 2008/0091042 A1    Apr. 17, 2008

Related U.S. Application Data

(63) Continuation of application No. PCT/IB2006/051451, filed on May 9, 2006.

(30) Foreign Application Priority Data

May 11, 2005    (WO) ................ PCT/IB2005/001310

(51) Int. Cl.
*C07C 69/76*    (2006.01)
*C07C 67/02*    (2006.01)
*C07C 41/00*    (2006.01)

(52) U.S. Cl. ......................................... 560/8; 568/326
(58) Field of Classification Search .................. 562/254; 560/8; 568/626

See application file for complete search history.

(56) References Cited

U.S. PATENT DOCUMENTS 3,548,006 A    12/1970    Scriabine ................... 260/599

2006/0069273 A1    3/2006    Shirai et al. .................. 549/462

FOREIGN PATENT DOCUMENTS

| EP | 1 574 509 A1 | 9/2005 |
| JP | 61161241 | 7/1986 |
| WO | WO 2004/054997 A1 | 7/2004 |

OTHER PUBLICATIONS

English Abstract: Brindaban C. Ranu, et al:., XP002405208, "Zinc Tetrafluoroborate-Catalyzed Efficient Conversion Of Aldehydes To Geminal Diacetates And Cyanoacetates" (2003).
English Abstract: Inoue, Katutaka et al., XP002405209, "Alkenylidene Diacetates" (1986).
Asit K. Chakraborti, et al., XP-002405203, "Copper(II) Tetrafluoroborate-Catalyzed Formation Of Aldehyde-1,1-Diacetates", Synthesis, No. 6, pp. 831-833, (2004).
Yi-Qun Li, XP001247839, "A Rapid And Convenient Synthesis Of 1,1-Diacetates From Aldehydes And Acetic Anhydride Catalyzed By PVC-FeCl₃ Catalyst" Synthetic Communications, vol. 30, No. 21, pp. 3913-3917, (2000).
Par Igor Scriabine, XP002977493, "No. 185—Nouveau procede de preparation des aldehydes dihydrocinnamiques", Mémoires Présentés A La Société Chimique, pp. 1194-1198, (1961).
R. Aquilar et al. "Friedel-Crafts Reaction of Activated Benzene Rings with Captodative and Electron-Deficient Alkenes. A One-Step Synthesis of the Natural Product Methyl 3-(2,4,5-Trimethoxyphenyl)propionate", Synthetic Communications, vol. 34, No. 15, pp. 2719-2735 (2004).

*Primary Examiner*—Sikarl A Witherspoon
(74) *Attorney, Agent, or Firm*—Winston & Strawn LLP

(57) ABSTRACT

The present invention relates to the field of organic synthesis. More particularly it provides a process for making aromatic non-conjugated enol esters or enol ethers from an aromatic compound or moiety and a protected enal compound or moiety, such as an acetal or an acylal. The reaction is promoted by a salt of formula $MX_{1-4}$, M representing a transition metal such as Zn or Fe and X representing a mono-anion, or by $BY_3$, wherein Y represents a fluoride or a phenyl group optionally substituted.

8 Claims, No Drawings

US 7,524,983 B2

CATALYTIC SCRIABINE REACTION

CROSS-REFERENCE TO RELATED APPLICATION(S)

This application is a continuation of International application PCT/IB2006/051451 filed on May 9, 2006, the entire content of which is expressly incorporated herein by reference thereto.

TECHNICAL FIELD

The present invention relates to the field of organic synthesis. More particularly it provides a process for making aromatic non-conjugated enol esters or enol ethers.

BACKGROUND

The Scriabine reaction consists of the reaction between an aromatic compound and an enal or the corresponding acylal (see I. Scriabine in *Bull. Soc. Chem. Fr.*, 1961, 1194). This reaction provides an access to the formation of dihydrocinnamic aldehyde derivatives. To the best of our knowledge, all the methods and examples reported in the literature concerning this reaction are at least steochiometric in an Al salt or in $TiCl_4$. For instance one may cite Aguillar et al. in *Synthetic Comm.* 2004, 2719.

It is therefore highly desirable to access such dihydrocinnamic aldehyde derivatives by using a catalyzed reaction, and, if possible, catalysts which are more environmentally friendly.

SUMMARY OF THE INVENTION

The present invention now relates to a process for making aromatic non-conjugated enol esters or enol ethers from an aromatic compound or moiety and a protected enal compound or moiety, such as an acetal or an acylal. The reaction is promoted by the use of catalytic amounts of certain metal derivatives.

DETAILED DESCRIPTION OF THE PREFERRED EMBODIMENTS

In order to solve the aforementioned problems, the present invention provides a process for making a compound of the formula

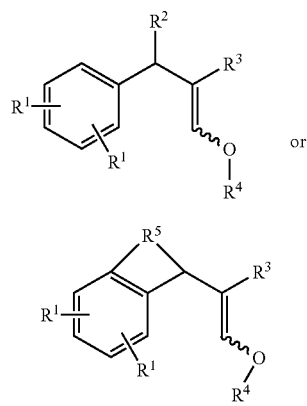

wherein the wavy line indicates that the double bond can be in a configuration E or Z or a mixture thereof;

each $R^1$ represents, taken separately, a hydrogen or halogen atom or a $C_1$-$C_6$ alkyl, alkoxy or amino group; or the two $R^1$, when taken together, represent a $C_3$-$C_{10}$ alkanediyl or alkenediyl group optionally substituted and optionally comprising one or two oxygen, sulfur or nitrogen atoms;

$R^2$ or $R^3$ represents, taken separately, a hydrogen atom or a $C_1$-$C_6$ alkyl group; $R^2$ and $R^3$, taken together, may represent a $C_3$-$C_{10}$ alkanediyl or alkenediyl group optionally substituted;

$R^4$ represents a $C_1$-$C_7$ alkyl or fluorinated alkyl group, a $C_7$-$C_{10}$ alkylaromatic optionally substituted, a $C_1$-$C_7$ acyl group, or a —COCOOH or —COCH$_2$COOH group; and $R^5$ represents a $C_2$-$C_9$ alkanediyl or alkenediyl group optionally substituted;

comprising the coupling of a compound of formula (II) with a compound of formula (III)

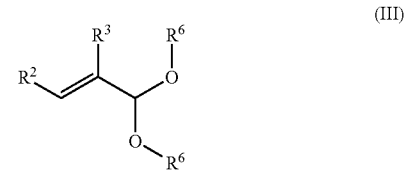

wherein $R^1$ to $R^3$ have the meaning indicated in formula (I) and each $R^6$, taken separately, represents a $C_1$-$C_7$ alkyl or fluorinated alkyl group, a $C_7$-$C_{10}$ alkylaromatic optionally substituted, a $C_1$-$C_7$ acyl group, or the $R^6$, taken together, represent a COCO or COCH$_2$CO group;

or, respectively, the cyclization of a compound of formula

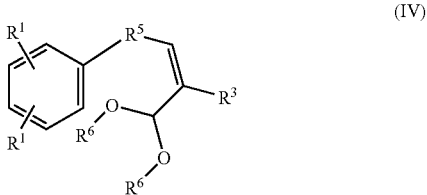

wherein $R^1$ and $R^3$ have the meaning indicated in formula (I), $R^6$ has the meaning indicated in formula (III), and $R^5$ has the meaning indicated in formula (I');

said processes being characterized in that it is carried out in the presence of a catalytic amount of at least one catalyst selected from the group consisting of a salt of formula $MX_n$, M representing a transition metal selected from the group consisting of Fe, Co, Ni, Cu and Zn, X representing a mono-anion and n is an integer from 1 to 3; and a boron compound of formula $BY_3$, wherein Y represents a fluoride or a phenyl group optionally substituted, and anyone of its adducts with a $C_2$-$C_{10}$ ether or a $C_1$-$C_8$ carboxylic acid.

Possible substituents of $R^1$ to $R^6$ are one, two or three halogen atoms or $OR^a$, $NR^a_2$ or $R^a$ groups, in which $R^a$ is a hydrogen atom or a $C_1$ to $C_{10}$ cyclic, linear or branched alkyl or alkenyl group, preferably a $C_1$ to $C_4$ linear or branched alkyl or alkenyl group.

Possible substituents of Y are one to five groups such as halide atoms or methyl or $CF_3$ groups.

It is also understood that, when $R^1$ are not hydrogen atoms, the compound of formula (I), or (I'), can be in the form of a mixture of isomers. For example, if the compound of formula (II) is methyl-benzene, then the compound (I) obtained can be in the form of a mixture of the ortho, or meta, and para isomers.

According to a first embodiment of the invention, the invention provides a process for making a compound of formula (I) or (I') wherein $R^4$ represents a $C_1$-$C_7$ alkyl group, a benzyl group optionally substituted or a $C_1$-$C_7$ acyl group.

According to a further embodiment, $R^2$ or $R^3$ may represent, taken separately, a hydrogen atom or a $C_1$-$C_4$ alkyl group; $R^2$ and $R^3$, taken together, may represent a $C_3$, $C_4$ or $C_{10}$ alkanediyl or alkenediyl group optionally substituted.

Moreover, each $R^1$ may represent, taken separately, a hydrogen or halogen atom or a $C_1$-$C_4$ alkyl or alkoxy group; or the two $R^1$, when taken together, represent a $C_3$-$C_5$ alkanediyl or alkenediyl group optionally substituted and optionally comprising one or two oxygen, sulfur or nitrogen atoms. According to a further embodiment, one, or the two, $R^1$ are not a hydrogen atom.

Furthermore, $R^5$ may also represent a $C_2$-$C_3$ alkanediyl or alkenediyl group optionally substituted.

It is understood that in such embodiment the starting material are the corresponding compounds of formula (II) and (III), or the corresponding compound of formula (IV).

According to a further embodiment of the present invention the invention provides a process for making a compound of formula (I) by the reaction of a compound of formula (II) with a compound of formula (III).

As non limiting examples of compound of formula (II) one may cite the following: benzene optionally substituted by one or two $C_1$-$C_4$ alkyl groups, 1,3-benzodioxole or indane optionally substituted by one or two $C_1$-$C_4$ alkyl groups, and in particular 1,1-dimethyl indane.

As non limiting examples of compound of formula (III) one may cite the following: acrolein diethyl acetal, acrolein diacetate, methacrolein diacetate, crotonaldehyde diacetate, tiglyl diacetate, cyclohexenyl carbaldehyde diacetate.

As mentioned above the invention process is carried out in the presence of at least one catalyst which is a salt of formula $MX_n$ or a compound of formula $BY_3$ and adducts thereof. Said catalyst can be in the anhydrous form or also in the hydrate form, except for those acids which are unstable in the presence of water. However the anhydrous form is preferred.

Furthermore, according to a particular embodiment of the invention the use of only one compound of formula $MX_n$ as catalysts is also preferred.

According to a particular embodiment of the invention, the catalyst is selected from the group consisting of $BY_3$ and adducts thereof, $FeX_3$, $CoX_2$, $NiX_2$, $ZnX_2$, $CuX_2$ and $CuX$.

According to a particular embodiment of the invention, the catalyst is selected from the group consisting of $BY_3$ and its adducts above mentioned, $FeX_3$, $NiX_2$, $ZnX_2$, and $CuX_2$ are particularly useful. Yet, more particularly, the catalyst may be a selected amongst $BY_3$ and its adducts above mentioned, $FeX_3$, and $ZnX_2$.

As mentioned above $BY_3$ can be used alone or in the form of one of its adducts with an ether or a carboxylic acid. Specific examples are the adducts of $BF_3$ with $Et_2O$, $Bu_2O$ or AcOH.

According to another embodiment of the invention, X is a mono-anion selected from the group consisting of acetylacetonate optionally substituted, $Cl^-$, $Br^-$, $C_{1-9}$ carboxylate, a $C_{1-10}$ sulphonate, $ClO_4^-$, $BF_4^-$, $PF_6^-$, $SbCl_6^-$, $AsCl_6^-$, $SbF_6^-$, $AsF_6^-$, $BR^7_4^-$, wherein $R^7$ is a phenyl group optionally substituted by one to five groups such as halide atoms or methyl or $CF_3$ groups, or a $R^8SO_3^-$, wherein $R^8$ is a chlorine or fluoride atom. In particular X can be selected from the group consisting of $Cl^-$, $Br^-$ and trifluoromethylsulfonate.

According to another embodiment of the invention, Y is F or $C_6H_5$.

According to a further embodiment of the invention, the catalyst is $BF_3$ and its adducts with AcOH, $FeCl_3$, $ZnBr_2$ or $ZnCl_2$.

The catalyst can be added to the reaction medium in a large range of concentrations. As non-limiting examples, one can cite catalyst concentrations ranging from 0.001 to 0.30 molar equivalents, relative to the molar amount of the starting compound (II) or (IV). Preferably, the catalyst concentrations will be comprised between 0.005 and 0.15 molar equivalents. It goes without saying that the optimum concentration of catalyst will depend on the nature of the catalyst and on the desired reaction time.

One can also cite catalyst concentrations ranging from 0.1 to 0.30 molar equivalents, relative to the molar amount of the starting compound (III). Preferably, the catalyst concentrations will be comprised between 0.01 and 0.10 molar equivalents. It goes without saying that the optimum concentration of catalyst will depend on the nature of the catalyst and on the desired reaction time.

It is useful here to mention that by "catalytic amount" we mean here any amount which allow the formation of the desired compound with a molar yield which exceeds the molar equivalents of catalyst added to the reaction mixture.

The temperature at which the invention's process can be carried out is typically between 0° C. and 180° C., more preferably in the range of between 15° C. and 100° C. Of course, a person skilled in the art is also able to select the preferred temperature as a function of the melting and boiling point of the starting and final products. Of course, a person skilled in the art is also able to select the preferred temperature as a function of the melting and boiling point of the starting and final products as well as of the solvent.

The process of the invention can be carried out in the presence or in the absence of solvent. As a person skilled in the art can anticipate, the presence of a solvent is mandatory only in the case in which the starting compound is a solid compound under the reaction conditions.

However, according to a preferred embodiment of the invention, and independently of the physical state of the starting compound, the process is advantageously carried out in the presence of a solvent. Preferably, said solvent is anhydrous or does not contain more than 1% w/w water.

Non-limiting examples of such a solvent are $C_4$-$C_8$ ethers, $C_3$-$C_6$ esters, $C_3$-$C_6$ amides, $C_6$-$C_9$ aromatic solvents, $C_5$-$C_7$ linear or branched or cyclic hydrocarbons, $C_1$-$C_2$ chlorinated solvents and mixtures thereof.

Furthermore, the reaction can also be carried out in the presence of a solvent belonging to the family of carboxylic anhydride of formula $R^9C(O)O(O)CR^9$, $R^9$ representing a $C_1$-$C_7$ alkyl group, a $C_7$-$C_{10}$ alkylaromatic optionally substituted, a $C_1$-$C_7$ acyl group, optionally containing the corresponding carboxylic acid $R^9COOH$. The optional substituents being the same as for $R_6$.

The compound of formula (III) or (IV) can be made and isolated according to any prior art method. Alternatively, compound (III) or (IV) can be also generated in situ, i.e. in the reaction medium just before its use, according to any know prior art method.

In particular, preferably the compound of formula (III) or (IV) is made or generated by a method using the corresponding enal as starting material.

Therefore, another object of the present invention is an invention's process, as defined above, further comprising the step of generating in situ the compound of formula (III) or (IV) starting from the corresponding enal of formula (V) or (V') respectively

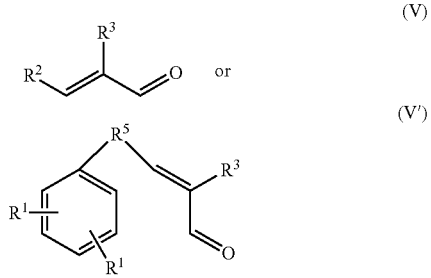

wherein $R^1$, $R^2$, $R^3$ and $R^5$ have the same meaning indicated above.

A process comprising the in situ generation of the compound of formula (III) or (I') is particularly useful when said compound (III) or (I') is an acetal or an acylal, the latter being a geminal dicarboxylate.

Now, when the compound of formula (II) is an acylal, we have also noticed that the catalysts that are able to promote the cyclization of the acylal are also useful to promote the conversion of the enal into the corresponding acylal.

Therefore, another object of the present invention, and in fact a particular embodiment of the above-mentioned process, is a process for making a compound of formula (I) or (I'), as defined above, comprising the step of reacting, in the presence of a catalyst as defined above, an enal of formula (V) or (V'), as defined above, with a carboxylic anhydride of formula $R^9C(O)O(O)CR^9$, wherein $R^9$ has the meaning indicated above.

EXAMPLES

The following examples are further illustrative of the present invention embodiments, and further demonstrate the advantages of the invention processes relative to prior art teachings. The abbreviations used in these examples have the usual meaning in the art and the temperatures are indicated in degrees centigrade (° C). The NMR spectral data were recorded in $CDCl_3$ at 400 MHz or 100 MHz for $^1H$ or $^{13}C$, respectively, the chemical displacements δ are indicated in ppm with respect to TMS as standard, and the coupling constants J are expressed in Hz. Each NMR spectra is provided in respect of the mayor isomer obtained, unless differently specified.

Example 1

Reaction between acrolein diacetate and 2-methyl indane

A solution of $FeCl_3.6H_2O$ in acetic acid (1.0M, 1.0 ml, 1 mmol) was added slowly dropwise to acetic anhydride (20.4 g, 200 mmol) at 5° C. The solution was allowed to warm to room temperature. A solution of acrolein (5.6 g, 100 mmol), in 2-methyl indane (20.0 g, 151 mmol) and dichloromethane (15 g) was added slowly dropwise to the anhydride solution, maintaining the temperature at about 15° C. The mixture was stirred at 20° C. for 4 hours then diluted with ethyl acetate (150 ml), and a saturated aqueous $NaHCO_3$ solution (50 ml) was added slowly dropwise. The aqueous phase was re-extracted with ethyl acetate (150 ml). The combined organic phases were washed with saturated aqueous $NaHCO_3$ solution (100 ml), brine (100 ml), dried over $MgSO_4$ and the solvents removed in vacuo. Further purification by Kugel-Rohr distillation at 150° C. ($2.9 \times 10^{-1}$ mbar) gave the desired enol acetate as a mixture of isomers (7.2 g, 30%).

$^1$H-NMR: 1.13 (d, J 6.2, 3H), 2.11 (s, 3H), 2.43-2.59 (m, 3H), 2.98-3.06 (m, 2H), 3.29 (d, J 8.2, 2H), 5.53-5.60 (m, 1H), 6.95 (d, J 7.2, 1H), 7.02 (s, 1H), 7.10 (d, J 7.7, 1H), 7.18 (dt, J 13.8, 1, 1H).

$^{13}$C-NMR: 20.7 (q), 20.9 (q), 33.5 (t), 34.65 (d), 40.7 (t), 41.0 (t), 114.2 (d), 124.4 (d), 126.0 (d), 136.0 (d), 137.5 (s), 141.8 (s), 144.2 (s), 168.2 (s).

Example 2

Reaction between acrolein diacetate and 2-methyl indane

A suspension of 2-methyl indane (2.6 g, 20 mmol) and acrolein diacetate (1.6 g, 10 mmol) and zinc bromide (0.25 g, 1 mmol) was stirred for 24 hours at ambient temperature. The reaction medium was then diluted with ethyl acetate (50 ml), and a saturated aqueous $NaHCO_3$ solution (50 ml) was added slowly dropwise. The aqueous phase was re-extracted with ethyl acetate (50 ml). The combined organic extracts were washed with saturated aqueous $NaHCO_3$ solution (50 ml), brine (50 ml), dried over $MgSO_4$, filtered and the solvents removed in vacuo. Further purification of the residue by KugelRohr distillation 180° C. ($8.0 \times 10^{-1}$ mbar) gave the enol acetate as a mixture of isomers (0.65 g, 30%) identical to that prepared above.

Example 3

Reaction between 2,2 dimethyl dihydrobenzofuran and acrolein diacetate

Zinc bromide (50 mg, 0.2 mmol) was suspended in a solution of acrolein diacetate (1.6 g, 10 mmol), 2,2 dimethyl dihydrobenzofuran (1.5 g, 10 mmol), in dichloromethane (5 g) and the stirred at ambient temperature for 24 hours. The reaction medium was then diluted with ethyl acetate (25 ml) and the saturated aqueous $NaHCO_3$ solution (20 ml) was added slowly dropwise. The aqueous phase was re-extracted with ethyl acetate (25 ml). The combined organic phase was washed with saturated aqueous $NaHCO_3$ solution (25 ml), brine (25 ml), then dried over $MgSO_4$, filtered and the solvents removed in vacuo. Further purification by KugelRohr distillation 160° C. ($3.3 \times 10^{-1}$ mbar) gave the desired enol acetate as a mixture of isomers (0.9 g, 37%).

$^1$H-NMR: 1.45 (s, 6H), 2.11 (s, 3H), 2.97 (s, 2H), 3.25 (d, J 7.7, 2H), 5.55 (dt, 12.3, 7.7, 1H), 6.64 (d, 8.2, 1H), 6.91 (d, J 8.2, 1H), 6.96 (s, 1H), 7.16 (d, 12.3, 1H).

$^{13}$C-NMR: 20.7 (q), 28.3 (q), 33.0 (t), 42.9 (t), 86.6 (s), 109.2 (d), 114.5 (d), 125.1 (d), 127.4 (s), 127.8 (d), 131.2 (s), 136.0 (d), 157.5 (s), 168.2 (s).

Example 4

Reaction between 2-methyl indane and methacrolein diacetate

BF$_3$ acetic acid complex (0.2 g, 1 mmol) was added to a stirred solution of 2-methyl indane (13.2 g, 100 mmol) and methacrolein diacetate (8.7 g, 50 mmol) heated at 60° C. The mixture was stirred at 60° C. for one hour, then cooled and diluted with ethyl acetate (50 ml), and saturated aqueous NaHCO$_3$ solution (50 ml) was added slowly dropwise. The aqueous phase was re-extracted with ethyl acetate (50 ml), the combined organic phase was washed with NaHCO$_3$ (100 ml), dried over MgSO$_4$, filtered and the solvents removed in vacuo. The residue was further purified by KugelRohr distillation 160° C. (6.0×10$^{-1}$ mbar) to give the enol acetate as a mixture of isomers (2.3 g, 19%).

$^1$H-NMR: (major isomer only) 1.13 (d, J 6.7, 3H), 1.60 (d, J 1.5, 3H), 2.14 (s, 3H), 2.44-2.59 (m, 3H), 2.97-3.05 (m, 2H), 3.22 (s, 2H), 6.93 (d, J 6.7, 1H), 6.99 (s, 1H), 7.05 (d, J 1.5, 1H), 7.08 (d, J 7.2, 1H).

$^{13}$C-NMR: 13.6 (q), 20.8 (q), 20.7 (q), 34.7 (d), 40.2 (t), 40.8 (t), 41.1 (t), 121.6 (s), 124.2 (d), 124.8 (d), 126.6 (d), 131.1 (d), 136.8 (s), 141.8 (s), 144.1 (s), 168.3 (s).

Example 5

Reaction between an aromatic and acroleine diacetate

A) General Procedure

A solution of FeCl$_3$.6H$_2$O in acetic acid (1.0M, 2-3 ml, 2-3 mmol, 5-10% mol) was added to a stirred solution of the indane derivative (35 mmol) acetic anhydride (2 g) and acrolein diacetate (6.5 g, 41 mmol) cooled to 0° C. Stirred for a further 60 minutes at ambient temperature, diluted with ethyl acetate (50 ml), and added saturated sodium bicarbonate (25 ml) slowly dropwise. The aqueous phase was re-extracted with ethyl acetate (50 ml), the combined organic phase was washed with bicarbonate (50 ml) then brine (50 ml), dried over magnesium sulfate, filtered and the solvents removed in vacuo. The crude product was purified by Kugelrohr distillation, firstly under moderate vacuum (5-10 mbar) to recover the indane, then under high vacuum (1.0-4.0×10$^{-1}$ mbar).

2-ethyl indane yield (18%), b.p 160° C. at 2.8×10$^{-1}$ mbar $^1$H-NMR: 0.96 (t, J 7.2, 3H), 1.50 (quintet, J 7.2, 2H), 2.10 (s, 3H), 2.34 (septet, J 7.2, 2H), 2.60-2.46 (m, 2H), 2.95-3.05 (m, 2H), 3.28 (d, J 7.7, 2H), 5.51-5.60 (m, 1H), 6.94 (d, J 7.7, 1H), 7.01 (s, 1H), 7.09 (d, J 7.7, 1H)7.17 (dt, J 12.3, 1.5, 1H)

$^{13}$C-NMR: 12.8 (q), 20.7 (q), 28.7 (t), 33.5 (t), 38.6 (t), 38.9 (t), 42.2 (d), 114.3 (d), 124.4 (d), 126.1 (d), 136.1 (d), 137.6 (s), 141.8 (s), 144.2 (s), 168.2.

2-propyl indane yield 1.4 g, 18%, b.p 150° C. at 2.5×10$^{-1}$ mbar)

$^1$H-NMR: 0.88-0.95 (m, 3H), 1.36-1.51 (m, 4H), 2.14 (s, 3H), 2.41-2.59 (m, 2H), 2.95-3.05 (m, 2H), 3.28 (d, J 7.7, 2H), 5.56 (dt, J 12.8, 7.2, 1H), 6.94 (d, J 7.7, 1H), 7.01 (s, 1H), 7.08-7.19 (m, 2H).

$^{13}$C-NMR: 14.3 (q), 20.7 (q), 21.5 (t), 33.5 (t), 38.1 (t), 38.9 (t), 40.20 (d), 114.3 (d), 124.4 (d), 126.0 (d), 126.1 (d), 136.1 (d), 137.5 (s), 141.8 (s), 143.7 (s), 144.2 (s), 168.2 (s).

2,2 dimethyl indane purified by column chromatography over silica (200 ml) with ether:pentane as eluant (1:19 then 1:9) gave the desired enol acetate (1.1 g, 14%).

$^1$H-NMR: 1.13 (s, 6H), 2.11 (s, 3H), 2.65-2.73 (m, 4H), 3.28 (d, J 7.7, 2H), 5.50-5.60 (m, 1H), 6.94 (d, J 7.7, 1H), 6.98 (s, 1H), 7.07 (d, J 7.7, 1H), 7.18 (dt, J 10.8, 1.5, 1H).

$^{13}$C-NMR: 20.8 (q), 28.8 (q), 33.5 (t), 40.2 (s), 47.4 (t), 47.7 (t), 114.3 (d), 124.7 (d), 126.0 (d), 136.1 (d), 137.5 (s), 141.6 (s), 144.0 (s), 168.2 (s).

cis trans 1,2 dimethyl indane yield 1.7 g, 28%, b.p 150° C. at 4.5×10$^{-1}$ mbar.

$^1$H-NMR: 0.94-1.08 (m, 3H), 1.10-1.14 (m, 3H), 1.16-1.20 (m, 1H), 1.25-1.29 (m, 1H), 2.11 (s, 3H), 2.47-2.58 (m, 3H), 2.90-2.99 (m, 2H), 3.12 (septet, J 6.7, 1H), 3.30 (t, J6.2, 2H), 5.55-5.59 (m, 1H), 6.94-7.20 (m, 4H).

$^{13}$C-NMR: 14.7 (q), 15.2 (q), 20.8 (q), 33.6 (t), 38.0 (d), 39.4 (t), 39.8 (t), 42.0 (d), 42.4 (d), 114.2 (d), 123.6 (d), 124.4 (d), 126.1 (d), 126.2 (d), 134.4 (s), 136.1 (d), 141.0 (s), 149.3 (s), 168.2 (s).

B) Tetrahydronapthalene

A solution of FeCl$_3$.6H$_2$O (1.0M in acetic acid, 1.0 ml, 1 mmol) was added to stirred solution of 1,2,3,4 tetrahydronaphthalene (21.65 g, 164 mmol), acetic anhydride (1.4 g, 13.6 mmol), acrolein diacetate (5.4 g, 34 mmol). The solution was stirred for a further 3 hours at ambient temperature, then poured into 5% sodium bicarbonate solution (200 ml), then the aqueous phase was extracted with ether (200 ml). The organic phase was washed with brine, dried over sodium sulfate, filtered and the solvents removed in vacuo. The residue was further purified by column chromatography on silica (300 ml) with cylohexane:ethyl acetate 19:1 and gave the enol acetates as a mixture of regio isomers (α and β (major) naphthyl, plus E and Z).

$^1$H NMR (both isomers): 1.70-1.86 (m, 4H), 2.11 (s, 3H), 2.64-2.80 (m, 4H), 3.21-3.29 (m, 2H), 5.55 (dt, J 12, 7, 1H), 6.82-7.25 (m, 4H).

$^{13}$C NMR(both isomers): 20.7 (q), 22.8 (t), 23.2 (t), 23.3 (t), 23.4 (t), 26.2 (t), 29.2 (t), 29.6 (t), 30.3 (t), 30.8 (t), 33.4 (t), 113.9 (d), 114.7 (d), 126.2 (d), 126.3 (d), 126.8 (d), 128.5 (d), 128.8 (d), 130.1 (d), 135.9 (s), 136.0 (s), 136.9 (d), 137.2 (s), 137.6 (s), 138.1 (s), 138.4 (d), 138.6 (d), 168.2 (s).

C) 1,1 Dimethyl indane

A solution of FeCl$_3$.6H$_2$O (1M in acetic acid, 0.3 ml) was added slowly drop wise to a stirred solution of 1,1 dimethyl indane (4.1 g, 28 mmol) acrolein diacetate (1.1 g, 7 mmol) and acetic anhydride (0.3 g, 2.8 mmol). After 2 hours stirring at room temperature, the mixture was poured into brine (50 ml) and the aqueous phase extracted with ether (100 ml). The organic phase was washed with sodium bicarbonate (50 ml), then brine (50 ml), dried over magnesium sulfate, filtered and the solvents removed in vacuo. The residue was further purified by Kugelrohr distillation, 120° C. at 10 mbar gave recovered 1,1 dimethyl indane (2.2 g) then distillation at 160° C. at 0.3 mbar gave the enol acetates as a mixture of isomers, (1.2 g, yield: 70%).

$^1$H NMR: 1.25 (s, 6H), 1.91 (t, J 7, 2H), 2.11 (s, 3H), 2.84 (t, J 7, 2H), 3.32 (d, J 7, 2H), 5.58 (dt, J 12, 7, 1H), 6.95 (s, 1H), 6.96 (d, J 8, 1H), 7.10 (d, J 8, 1H), 7.18 (dt, J 12, 8, 1H).

$^{13}$NMR: 20.7 (q), 28.6 (q), 29.6 (q), 33.6 (t), 41.6 (t), 43.9 (t), 114.2 (d), 121.9 (d), 124.4 (d), 126.3 (d), 136.1 (d), 137.8 (s), 140.8 (s), 153.0 (s),168.1 (s)

Example 6

Reaction between Tert-butyl benzene and acrolein diacetate

A solution of $FeCl_3.6H_2O$ (1M in acetic acid, 2.5 ml, 2.5 mmol) was added slowly drop wise to a stirred solution of tert-butyl benzene (55 g, 410 mmol) acrolein diacetate (13.5 g, 85 mmol) and acetic anhydride (3.5 g, 34.3 mmol). After 3 hours stirring at room temperature, the mixture was poured into brine (50 ml) and the aqueous phase extracted with ether (2×100 ml). The organic phase was washed with sodium bicarbonate (50 ml), then brine (50 ml), dried over magnesium sulfate, filtered and the solvents removed in vacuo. The residue was further purified by column chromatography on silica (500 ml) with cyclohexane then 5:95 ethyl acetate: cyclohexane gave recovered tert-butyl benzene then the enol acetates as a mixture of meta and para isomers, (2.7 g, yield: 14%).

$^1$H NMR: (both isomers) 1.31 (s, 9H), 2.11 (s, 3H), 3.30 (d, J 8, 2H) 5.58 (dt, J 12, 8, 1H), 7.12-7.21 (m, 4H), 7.32 (d, J 8, 1H).

$^{13}$NMR: 20.7 (q), 30.1 (s), 31.4 (q), 33.0 (t), 34.4 (s), 112.6 (d), 113.9 (d), 125.4 (d), 127.9 (d), 128.0 (d), 134.5 (d), 136.2 (d), 136.7 (d), 136.9 (d), 149.0 (s), 149.2 (s), 168.0 (s), 168.2 (s).

Example 7

Reaction between Sec-butyl benzene and acrolein diacetate

A solution of $FeCl_3.6H_2O$ (1M in acetic acid, 0.5 ml, 0.5 mmol) was added slowly drop wise to a stirred solution of sec-butyl benzene (11 g, 82 mmol) acrolein diacetate (2.7 g, 17 mmol) and acetic anhydride (0.7 g, 6.8 mmol) in dichloromethane (15 ml). After 3 hours stirring at room temperature, the mixture was poured into saturated sodium bicarbonate (50 ml) and the aqueous phase extracted with ether (100 ml). The organic phase was washed with saturated sodium bicarbonate (50 ml), then brine (50 ml), dried over magnesium sulfate, filtered and the solvents removed in vacuo. The residue was further purified by column chromatography on silica (500 ml) with cyclohexane then 5:95 ethyl acetate: cyclohexane gave recovered sec-butyl benzene then the enol acetate as a mixture of isomers, (1.3 g, yield: 33%).

$^1$H NMR: 0.81 (t, J 7, 3H), 1.21 (d, J 7, 3H), 1.57 (q, J 7, 2H), 2.11 (s, 3H), 2.57 (s, J7, 1H), 3.30 (dd, J 8, 1, 2H), 5.65-5.52 (m, 1H), 7.10-7.25 (m, 5H).

$^{13}$NMR: 12.2 (q), 20.7 (q), 21.8 (q), 31.2 (t), 33.19 (t), 41.3 (d), 114.0 (d), 127.2 (d), 128.2 (d), 136.2 (d), 137.0 (s), 168.2 (s).

Example 8

Reaction between 1,3 benzodioxole and methacrolein diacetate

Zinc chloride (0.14 g, 1 mmol, 10 mol %) was added to a stirred solution of 1,3 methylenedioxy benzene (2.4 g, 20 mmol) and methacrolein diacetate (1.72 g, 10 mmol) at ambient temperature. The solution was stirred at ambient temperature for a further 48 hours. The solution was diluted with ethyl acetate (59 ml), and sodium bicarbonate 5% (50 ml), the aqueous phase was re-extracted with ethyl acetate (50 ml), the organic phase was washed with brine (50 ml), dried over magnesium sulfate, filtered and the solvents removed in vacuo. The residue was further purified by column chromatography over silica (50 ml), with cylohexane then 1:19 then 1:9 ethyl acetate:cylohexane as eluant. The desired product 1.23 g was further purified by Kugelrohr distillation 125° C. at 3.5×10$^{-2}$ mbar, to give the enol acetate, (1.0 g, yield: 53%).

$^1$H NMR: 1.58 (d, J 1.5, 3H), 2.14 (s, 3H), 3.17 (s, 2H), 5.91 (s, 2H), 6.63 (dd, J 8, 1.5, 1H), 6.67 (d, J 1.5, 1H), 6.72 (d, J 8, 1H), 7.02 (d, J 1.5, 1H).

$^{13}$NMR: 13.4 (q), 20.8 (q), 40.0 t), 100.9 (t), 108.0 (d), 109.0 (d), 121.3 (s), 121.7 (d) 131.2 (d), 132.8 (s), 146.1 (s), 147.7 (s) and 168.3 (s).

Example 9

Reaction between anisole and tiglic diacetate

Zinc chloride (0.14 g, 1 mmol), was added to a solution of anisole (2.16 g, 20 mmol) and tiglic diacetate (1.86 g, 10 mmol), and the mixture stirred at ambient temperature for 3 hours. The solution was diluted with ethyl acetate (25 ml) and saturated sodium bicarbonate (50 ml), the aqueous phase was re-extracted with ethyl acetate (25 ml) the combined organic phases were washed with brine, dried over magnesium sulfate, filtered and the solvents removed in vacuo. Further purification by column chromatography over silica (50 ml) with cyclohexane, then 1:19, then 1:9 ethyl acetate cyclohexane gave the enol acetate as a mixture of isomers. Further purification by Kugelrohr distillation 125° C. at 3.5×10$^{-2}$ mbar gave the enol acetate as a mixture of isomers, (1.2 g, yield: 51%).

$^1$H NMR: 1.37 (d, J 7, 3H), 1.51 (d 1.5, 3H), 2.13 (s, 3H), 3.37 (q, J 7, 1H), 3.77 (s, 3H), 6.83 (d, J 9, 2H), 7.13 (d, J 9, 2H), 7.13 (m, 1H).

$^{13}$C NMR: 12.1 (q), 19.3 (q), 20.8 (q), 42.5 (d), 55.2 (q), 113.6 (d), 128.3 (d), 130.6 (d), 136.2 (s), 158.0 (s), 168.3 (s).

Example 10

Reaction between 2-methyl indane and crotonaldehyde diacetate

Acetic anhydride (5 g, 49 mmol) was added to a suspension of $FeCl_3.6H_2O$ (1.08 g, 4 mmol) and 2-methyl indane (26.4 g, 200 mmol), after 5 mins crotonaldehyde diacetate (6.88 g, 40 mmol) was added slowly drop wise. The mixture was stirred for a further 7 hours, then poured into brine (50 ml), extracted with ether (100 ml), washed the organic extract with sodium bicarbonate (100 ml), then brine (50 ml), dried over magnesium sulfate, filtered and the solvents removed in vacuo. The residue was further purified by distillation, 65° C. at 10 mbar, gave the recovered 2-methyl indane then distillation of the residue 170° C. at 0.1 mbar gave the enol acetate as a mixture of isomers, (4.3 g, yield: 44%).

$^1$H NMR (for both major isomers): 1.11-1.17 (m, 3H), 1.34 (d, J 7, 3/2H), 1.36 (d, J 6.6, 3/2H), 2.07 (s, 3/3H), 2.09 (s, 3/3H), 2.15 (s, 3/3H), 2.45-2.58 (m, 3H), 2.96-3.08 (m, 2H), 3.45 (quintet, J 7, 1/2H), 3.96 (m, 1/2H), 5.03 (dd, J 10, 7, 1/2H), 5.61 (dd, J 12.8, 7, 1/2H), 6.94-7.20 (m, 4H).

$^{13}$C NMR (for both major isomers): 20.7 (q), 20.9 (q), 22.0 (q), 34.5 (d), 34.8 (d), 40.8 (t), 41.1 (t), 119.3 (d), 123.0 (d), 124.4 (d), 124.8 (d), 126.0 (d), 132.6 (d), 135.0 (d), 141.9 (s), 143.5 (s), 144.2 (d), 168.7 (s).

Example 11

Reaction between anisole and cyclohexenyl carbaldehyde diacetate

A solution of $FeCl_3.6H_2O$ (1M in acetic acid, 0.31 ml) was added slowly dropwise to a stirred solution of anisole (5.53 g, 51 mmol) cyclohexane carbaldehyde diacetate (2.3 g, 10.8 mmol) and acetic anhydride (0.46 g, 4.5 mmol). After 4 hours stirring at room temperature, the mixture was poured into brine (50 ml) and the aqueous phase extracted with ether (2×100 ml). The organic phase was washed with sodium bicarbonate (50 ml), then brine (50 ml), dried over magnesium sulfate, filtered and the solvents removed in vacuo. The residue was further purified by column chromatography on silica (500 ml) with cyclohexane then 5:95 ethyl acetate: cyclohexane gave the enol acetates as a mixture of isomers, (2.57 g, 91%). MS: M(+) 260, 200, 172, 169, 121, 108, 43 m/z.

Example 12

Intramolecular Cyclization of 6-phenyl-hex-2-enal

A solution of $FeCl_3.6H_2O$ (0.112M in acetic anhydride, 1.2 ml, 0.134 mmol) was added slowly dropwise to 6-phenyl-hex-2-enal (1.8 g, 10 mmol) with stirring at 5° C. over 15 minutes. The reaction mixture was allowed to warm slowly to ambient temperature and stirred for a further 20 hours. The dark mixture was poured into saturated sodium bicarbonate solution, then extracted with ether (3×10 ml). The combined organic phase was dried over sodium sulfate, filtered and the solvents removed in vacuo. The residue was rapidly distilled by Kugelrohr 140-170° C. at $5.0 \ 10^{-2}$ mbar to afford the enol acetates (2-(1,2,3,4-tetrahydro-1-naphthalenyl)vinyl acetate) as a mixture of E/Z isomers, 1.8 g, 83%.

E isomer:
$^1H$ NMR: 1.68-1.70 (m, 1H), 1.71-1.80 (m, 1H), 1.86-2.01 (m, 2H), 2.12 (s, 3H), 2.72-2.84 (m, 2H), 3.41-3.49 (m, 1H), 5.49 (dd, J 13, 9, 1H), 7.05-7.19 (m, 5H).
$^{13}$NMR: 20.7 (q), 20.9 (t), 29.6 (t), 30.8 (t), 37.8 (d), 119.5 (d), 125.7 (d), 126.2 (d), 129.2 (d), 129.3 (d), 136.1 (d), 136.9 (s), 137.9 (s), 168.2 (s).

Z isomer:
$^1H$ NMR: 1.54-1.64 (m, 1H), 1.73-1.83 (m, 1H), 1.89-2.03 (m, 2H), 2.18 (s, 3H), 2.75-2.86 (m, 2H), 3.99-4.06 (m, 1H), 4.98 (dd, J 10, 6, 1H), 7.05-7.14 (m, 4H), 7.16 (d, J 6, 1H).
$^{13}$NMR: 20.8 (q), 21.5 (t), 29.6 (t), 30.1 (t), 34.9 (d), 118.7 (d), 125.8 (d), 126.0 (d), 128.9 (d), 129.1 (d), 133.9 (d), 136.8 (s), 138.5 (s), 168.2 (s).

Example 13

Intramolecular Cyclization of 4-methyl-6-phenyl-hex-2-enal

A solution of $FeCl_3.6H_2O$ (0.112M in acetic anhydride, 1.2 ml, 0.134 mmol) was added slowly dropwise to 4-methyl-6-phenyl-hex-2-enal (2.0 g, 10.1 mmol) with stirring at 5° C. over 15 minutes. The reaction mixture was allowed to warm slowly to ambient temperature and stirred for a further 20 hours. The dark mixture was poured into saturated sodium bicarbonate solution, then extracted with ether (3×10 ml). The combined organic phase was dried over sodium sulfate, filtered and the solvents removed in vacuo. The residue was rapidly distilled by Kugelrohr 150-180° C. at $5.0 \ 10^{-2}$ mbar to afford the enol acetates (2-(2-methyl-1,2,3,4-tetrahydro-1-naphthalenyl)vinyl acetate) as a mixture of isomers, 2:2:1:1, 1.9 g, 82%.

$^1H$ NMR (major isomers): 0.96 (d, J 3, 3/2H), 0.98 (d, J 2.5, 3/2 H), 1.41-1.80 (m, 2H), 1.89-2.08 (m, 1H), 2.08 (s, 3/2H), 2.19 (s, 3/2H), 2.80-2.85 (m, 2H), 3.34 (dd, J 9.7, 5, 1/2H), 4.02 (dd, J 10, 5, 1/2H), 4.90 (dd, J 10.7, 6.6, 1/2H), 5.49 (dd, J 12.3, 10.2, 1/2H), 7.06-7.31 (m, 5H).
$^{13}$C NMR(major isomers): 18.3 (q), 18.9 (q), 20.7 (q), 20.8 (q), 26.7 (t), 26.9 (t), 28.7 (t), 28.8 (t), 32.1 (d), 32.4 (d), 116.0 (d), 117.8 (d), 125.9 (d), 126.0 (d), 128.9 (d), 129.7 (d), 136.9 (s), 138.5 (s), 168.1 (d), 168.2 (d) ppm.

What is claimed is:

1. A process for making a compound of formula

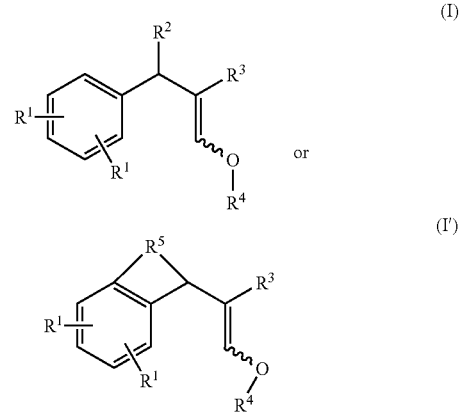

wherein the wavy line indicates that the double bond can be in a configuration E or Z or a mixture thereof;

the two $R^1$, taken separately, one represents a hydrogen atom and the other a $C_1$-$C_4$ alkyl group; or the two $R^1$, when taken together, represent a $C_3$-$C_5$ alkanediyl or alkenediyl group optionally substituted;

$R^2$ or $R^3$ represents, taken separately, a hydrogen atom or a $C_1$-$C_6$ alkyl group; $R^2$ and $R^3$, taken together, may represent a $C_3$-$C_{10}$ alkanediyl or alkenediyl group optionally substituted;

$R^4$ represents a $C_1$-$C_7$ alkyl or fluorinated alkyl group, a $C_7$-$C_{10}$ alkylaromatic optionally substituted, a $C_1$-$C_7$ acyl group, or a —COCOOH or —COCH$_2$COOH group; and $R^5$ represents a $C_2$-$C_9$ alkanediyl or alkenediyl group optionally substituted;

comprising the coupling of a compound of formula (II) with a compound of formula (III)

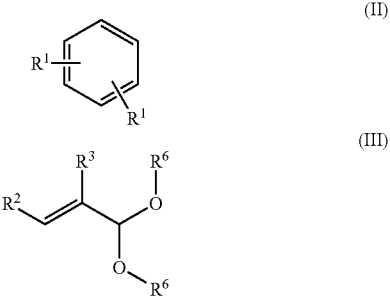

wherein $R^1$ to $R^3$ have the meaning indicated in formula (I) and each $R^6$, taken separately, represents a $C_1$-$C_7$ alkyl or fluorinated alkyl group, a $C_7$-$C_{10}$ alkylaromatic optionally substituted, a $C_1$-$C_7$ acyl group, or the $R^6$, taken together, represent a COCO or COCH$_2$CO group;

or, respectively, cyclizing a compound of formula

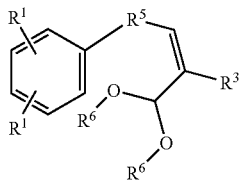

(IV)

wherein $R^1$ and $R^3$ have the meaning indicated in formula (I), $R^6$ have the meaning indicated in formula (III), and $R^5$ have the meaning indicated in formula (I');

said processes being characterized in that it is carried out in the presence of a catalytic amount of at least one catalyst selected from the group consisting of a salt of formula $MX_n$, M representing a transition metal selected from the group consisting of Fe, Co, Ni, Cu and Zn, X representing a mono-anion and n is an integer from 1 to 3; and a boron compound of formula $BY_3$, wherein Y represents a fluoride or a phenyl group optionally substituted, and any one of its adducts with a $C_2$-$C_{10}$ ether or a $C_1$-$C_8$ carboxylic acid.

2. A process according to claim 1, wherein the compound of formula (II) is a benzene optionally substituted by one or two $C_1$-$C_4$ alkyl groups or an indane optionally substituted by one or two $C_1$-$C_4$ alkyl groups.

3. A process according to claim 1, wherein the compound of formula (III) is acrolein diethyl acetal, acrolein diacetate, methacrolein diacetate, crotonaldehyde diacetate, tiglyl diacetate, cyclohexenyl carbaldehyde diacetate.

4. A process according to claim 1, wherein the catalyst is selected from the group consisting of $BY_3$ and adducts thereof, $FeX_3$, $CoX_2$, $NiX_2$, $ZnX_2$, $CuX_2$ and CuX.

5. A process according to claim 1, wherein the catalyst is selected from the group consisting of $BY_3$ and its adducts, $FeX_3$, and $ZnX_2$.

6. A process according to claim 1, wherein X is a monoanion selected from the group consisting of acetylacetonate optionally substituted, Cl$^-$, Br$^-$, $C_{1-9}$ carboxylate, a $C_{1-10}$ sulphonate, $ClO_4^-$, $BF_4{-\!\!-}$, $PF_6{-\!\!-}$, $SbCl_6{-\!\!-}$, $AsCl_6{-\!\!-}$, $SbF_6{-\!\!-}$, $AsF_6{-\!\!-}$, $BR^7{_4}{-\!\!-}$, wherein $R^7$ is a phenyl group optionally substituted by one to five groups such as halide atoms or methyl or $CF_3$ groups, or a $R^8SO_3^-$, wherein $R^8$ is a chlorine or fluoride atom.

7. A process according to claim 1, wherein X is Cl$^-$, Br$^-$ or trifluoromethylsulfonate.

8. The process according to claim 1, wherein the catalyst is $BF_3$ and its adducts with AcOH, $FeCl_3$, $ZnBr_2$ or $ZnCl_2$.

* * * * *

UNITED STATES PATENT AND TRADEMARK OFFICE
CERTIFICATE OF CORRECTION

PATENT NO. : 7,524,983 B2
APPLICATION NO. : 11/861078
DATED : April 28, 2009
INVENTOR(S) : Snowden et al.

It is certified that error appears in the above-identified patent and that said Letters Patent is hereby corrected as shown below:

Column 4:
Lines 8-9, delete "$BF_4$—, $PF_6$—, $SbCl_6$—, $AsCl_6$—, $SbF_6$—, $AsF_6$—," and insert -- $BF_4^-$, $PF_6^-$, $SbCl_6^-$, $AsCl_6^-$, $SbF_6^-$, $AsF_6^-$, --.

Column 12:
Line 66 (claim 1, last line in column 12), delete "cyclizing" and insert -- the cyclisation of --.

Column 14:
Lines 16-17 (claim 6, lines 4-5), delete "$BF_4$—, $PF_6$—, $SbCl_6$—, $AsCl_6$—, $SbF_6$—, $AsF_6$—, $BR^7_4$—" and insert -- $BF_4^-$, $PF_6^-$, $SbCl_6^-$, $AsCl_6^-$, $SbF_6^-$, $AsF_6^-$, $BR^7_4{}^-$ --.
Line 23 (claim 8, line 1), before "process" delete "The" and insert -- A --.

Signed and Sealed this

Ninth Day of June, 2009

JOHN DOLL
*Acting Director of the United States Patent and Trademark Office*